US012661372B2

(12) United States Patent (10) Patent No.: US 12,661,372 B2
Arshintseva et al. (45) Date of Patent: Jun. 23, 2026

(54) PHARMACEUTICAL COMPOSITION COMPRISING POLOXAMER 188 FOR IMPROVING THE FILTERING FUNCTION OF KIDNEYS

(71) Applicants: Elena Valentinovna Arshintseva, Republic of Mordovia (RU); Sergei Yurevich Pushkin, Noginsk-9 (RU)

(72) Inventors: Elena Valentinovna Arshintseva, Republic of Mordovia (RU); Sergei Yurevich Pushkin, Noginsk-9 (RU)

( * ) Notice: Subject to any disclaimer, the term of this patent is extended or adjusted under 35 U.S.C. 154(b) by 253 days.

(21) Appl. No.: 18/682,135

(22) PCT Filed: Aug. 12, 2021

(86) PCT No.: PCT/RU2021/000347
§ 371 (c)(1),
(2) Date: Feb. 8, 2024

(87) PCT Pub. No.: WO2023/018347
PCT Pub. Date: Feb. 16, 2023

(65) Prior Publication Data
US 2024/0358742 A1 Oct. 31, 2024

(51) Int. Cl.
*A61K 31/765* (2006.01)
*A61P 13/12* (2006.01)
(52) U.S. Cl.
CPC ............ *A61K 31/765* (2013.01); *A61P 13/12* (2018.01)

(58) Field of Classification Search
CPC .............................. A61K 31/765; A61P 13/12
See application file for complete search history.

(56) References Cited

U.S. PATENT DOCUMENTS

| 10,195,238 B2 | 2/2019 | Tai et al. |
| 2007/0237740 A1 | 10/2007 | Reddington et al. |
| 2016/0000823 A1* | 1/2016 | Emanuele ............ A61K 38/482 |
| | | 424/78.38 |

FOREIGN PATENT DOCUMENTS

| WO | 2016/007542 | 1/2016 |
| WO | 2020/122745 | 6/2020 |

* cited by examiner

*Primary Examiner* — Zohreh A Fay
(74) *Attorney, Agent, or Firm* — Soroker Nordman Riba

(57) ABSTRACT

The invention relates to the field of medicine and veterinary medicine, in particular to a pharmaceutical composition for improving the filtering function of kidneys. A pharmaceutical composition for improving the filtering function of the kidneys of a subject, comprising poloxamer-188 as a pharmacologically active substance and at least one excipient. A pharmaceutical composition for improving the filtering function of kidneys is developed, the components of which ensure the achievement of the technical result consisting in a substantial reduction in side effects resulting from its use in comparison with the closest analogue.

4 Claims, No Drawings

PHARMACEUTICAL COMPOSITION COMPRISING POLOXAMER 188 FOR IMPROVING THE FILTERING FUNCTION OF KIDNEYS

The invention relates to the field of medicine and veterinary medicine, in particular to a pharmaceutical composition for improving the filtering function of kidneys.

At present, kidney diseases around the world are not only a medical problem, but also a public health problem in general. Unfortunately, it is beginning to take on epidemic proportions. It is assumed that about 10% of the world's population suffer from kidney diseases. Kidneys perform such important functions for the body as cleansing the body of toxic substances; removal of excess fluid; production of the hormone erythropoietin needed to maintain a normal level of haemoglobin; maintaining blood pressure etc. Meanwhile, their major function is filtering. In kidney diseases said function is impaired, which is manifested by the accumulation of metabolic products in the blood, such as urea and creatinine. It should be noted that many factors, such as congenital developmental anomalies, hypothermia, overflow of the bladder, chronic-fatigue build-up, metabolic disorders, dramatic weight loss, obesity, chemotherapy, excessive alcohol consumption, xanthine oxidase deficiency Considering that poloxamer-188 binds to damaged cell membranes in areas with low lipid density, as well as contributes to stability and restores membrane barrier function, the authors of the present invention made an assumption that a pharmaceutical composition comprising poloxamer-188 will be used to improve the filtration function of the kidneys of a subject.

It is known that poloxamers are polyoxyethylene and polyoxypropylene block copolymers, which are used not only as excipients, but also as drug substances that have useful biological properties. Poloxamer has the most widespread use as an emulsifier for perfluoroorganic compound based emulsions for intravenous administration, as well as a stabilizer that provides transparency to elixirs and syrups. In addition, poloxamer is used as a wetting agent in eye drops, ointments, gels and as a binding agent in tablets. Poloxamers are also used for the treatment of pathological hydrophobic interactions in the blood and in other biological fluids, since they improve blood flow and reduce the adhesion of macromolecules and cells. It should be noted that there are several types of commercial-grade poloxamers, which are known under different trade names and differ from each other in molecular mass, in the amount of polyoxyethylene (POE) and polyoxypropylene (POP) blocks in the molecule. The characteristics of said commercial-grade poloxamers-188 are given in Table 1.

TABLE 1

| Characteristics of commercial-grade poloxamers-188 | | | |
|---|---|---|---|
| The classification of a poloxamer according to USP (United States Pharmacopoeia) | Molecular weight, Da | Number of oxypropylene blocks, % | Some examples of trade names of poloxamers |
| Poloxamer 188 | 7680-9510[1] | 16.3-20.1 | Pluronic F68, Lutrol 68, Kolliphor 188 (produced by BASF), Synperonic PE/F68 (produced by CRODA) |

Note:
[1]information from United States Pharmacopoeia.

etc., and a wide range of diseases, including diabetes mellitus and hypertension, lay behind the impairment of the filtering function of kidneys.

The drug "Lespefril" produced by CJSC "VIFITEKH" (the Russian Federation) is known in the prior art, which includes shoots of *Lespedeza bicolor*, ethyl alcohol 95%, purified water and anise oil (registration number in the State Register of Medicines of the Russian Federation LS-000571) and is chosen as the closest analogue. Said medicinal product promotes an increase in glomerular filtration, reduces azotemia (promotes the excretion of urea, creatinine and uric acid from the body), increases urine output.

It should be noted that excretion of sodium from the body during its administration, which can lead to hyponatremia, is among the disadvantages of said medicinal product.

The problem to be solved by the present invention is to develop a pharmaceutical composition for improving the filtering function of kidneys, the components of which will ensure the achievement of the technical result consisting in a substantial reduction in side effects resulting from its use in comparison with the closest analogue.

The problem posed is solved by developing a pharmaceutical composition for improving the filtering function of the kidneys of a subject, comprising poloxamer-188 as a pharmacologically active substance and at least one excipient.

At the same time, poloxamer-188 also comprises both the molecules sized less than 4500 Da and the molecules sized more than 13000 Da (M. Emanuele and B. Balasubramaniam, Differential Effects of Commercial-Grade and Purified Poloxamer 188 on Renal Function, Drugs in R D. 2014 June: 14 (2): 73-83).

Poloxamer-188 is a non-ionic amphiphilic copolymer consisting of a hydrophobic polyoxypropylene central chain flanked at both ends with hydrophilic polyoxyethylene. Its average molecular mass is about 8500 kDa. Furthermore, it is known that poloxamer-188 belongs to low toxic substances and does not have side effects when administered to a subject's body.

As used herein, the term "improving the filtering function of the kidneys in a subject" refers to improving certain indicators of the function of the kidneys of a subject, namely, increasing daily urine output of the subject, decreasing blood creatinine and urea level of the subject, and increasing glomerular filtration rate of the subject. It should be noted that said indicators depend on the sex and age of the subject.

As used herein, the term "daily urine output" refers to the volume of urine excreted by the subject over 24 hours.

As used herein, the term "glomerular filtration rate" refers to the volume of blood plasma purified from the capillaries of the glomeruli of the kidney into Bowman's capsule per unit of time.

As used herein, the term "creatinine level" refers to the quantitative content of creatinine in blood plasma. Creatinine is an end product of the breakdown of creatine, which plays an important role in the energy metabolism of muscle tissue and other tissues. Under normal conditions, creatinine is freely filtered in the renal glomeruli and then, without undergoing reabsorption or further secretion in the tubules, is almost completely excreted with the urine from the body. Thus, an increase in creatinine concentration in serum is due to a decrease in the level of renal filtration and is one of the key markers of kidney disease.

Another key marker to be noted as well is the level of urea, an increase in which in blood serum suggests an impairment of glomerular filtration and is indicative of the presence of a kidney disease. Urea is one of the end products of protein metabolism, which comprises nitrogen. It is produced in the liver, transported by the blood to the kidneys, where it is filtered through the renal glomeruli, and then excreted with the urine from the body (approximately 85% of urea is excreted from the body when the blood is filtered in the kidneys). In this case, a rapid degradation of proteins and damage to kidneys rapidly raise the level of urea in the blood.

In a preferred embodiment, the pharmaceutical composition is in the form of a solution for oral administration.

Formulations of pharmaceutical compositions of the present invention suitable for oral administration may be provided in the form of aqueous solutions by using an appropriate solvent. In this case, water for injection or purified water are the preferred solvents. Additionally, the aqueous formulations may include metal salts such as sodium chloride, potassium chloride, magnesium chloride, as well as the following additional components: glucose, ascorbic acid, inosine. The quantitative content of additional components in said composition is: for sodium chloride—0.3-0.9 wt %, for potassium chloride—0.03-0.04 wt %, for magnesium chloride—0.01-0.02 wt %, for glucose—0.5-10 wt %, for ascorbic acid—0.1-1.0 wt %, and for inosine—0.1-1.0 wt %.

Solutions comprising poloxamer-188 can be packaged in containers, such as vials.

Formulations of pharmaceutical compositions according to the present invention can be prepared by any method known in the pharmaceutical art.

In a preferred embodiment, the single daily dose of poloxamer-188 is from 8.6 to 90.0 mg/kg of body weight of the subject.

Also, in a preferred embodiment of the claimed invention, the pharmaceutical composition is administered to a subject which is a mammal.

In this case, in a preferred embodiment, the mammal is a human and "companion animals". The term "companion animal" means any domestic animal, including, but not limited to, cats, dogs, rabbits, guinea pigs, ferrets, hamsters, mice, horses, cows, goats, pigs. Preferred mammals are humans, dogs, cats and rabbits.

Preferably, the pharmaceutical composition is administered to a mammal on a daily basis for 6 months.

Examples of improving the filtering function of the kidneys by using a pharmaceutical composition comprising poloxamer-188 in humans are given below. In this case, trade marks of Poloxamer-188 such as Kolliphor P188 were used.

EXAMPLE 1

Patient A., a boy, 9 years old. Diagnosis: hypoplasia of the left kidney, granular left kidney, reflux nephropathy on the left, vicarious hypertrophy of the right kidney. The daily urine output was 600 ml, which is significantly lower than the normal range for the indicator, which is 900-1200 ml. Oral treatment with an aqueous saline solution of poloxamer-188 (Kolliphor P188) at a dosage of 90.0 mg/kg once a day for 6 months was prescribed. After using the above pharmaceutical composition, the daily urine output increased to 1000 ml, which is a normal value for said indicator.

EXAMPLE 2

Patient N., a woman, 69 years old. Diagnosis: chronic pyelonephritis. A test for glomerular filtration rate and the level of creatinine in the blood was conducted. As a result of the test conducted, it was found that: the glomerular filtration rate was 53 ml/min, while the normal range for this indicator being >60 ml/min, which is significantly lower than the normal range, and the level of creatinine in the blood was 95 µmol/l, while the normal range being 58-110 µmol/l for women above 60 years of age, which is a normal value for said indicator. Oral treatment with an aqueous saline solution of poloxamer-188 (Kolliphor P188) at a dosage of 8.6 mg/kg once a day for 6 months was prescribed. After using the above pharmaceutical composition, the glomerular filtration rate was 79 ml/min, and the creatinine level was 69 µmol/l, which are the normal values for said indicators.

EXAMPLE 3

Patient R., a man, 67 years old. Diagnosis: chronic renal failure. A test for glomerular filtration rate, the level of creatinine and urea in the blood was conducted. As a result of the test conducted, it was found that: the glomerular filtration rate was 38 ml/min, while the normal range for this indicator being >60 ml/min, which is significantly lower than the normal range, the level of creatinine in the blood was 159 ml/min per 1.73 sq. m., while the normal range for this indicator being 58-110 ml/min per 1.73 sq. m., which is significantly higher than the normal range, the level of urea in the blood was 10.6 mmol/l, while the normal range for this indicator being 3.2-7.1 mmol/l. Oral treatment with an aqueous saline solution of poloxamer-188 (Kolliphor P188) at a dosage of 22.86 mg/kg once a day for 6 months was prescribed. After using the above pharmaceutical composition, the glomerular filtration rate was 77 ml/min, the level of creatinine and urea in the blood was 89 ml/min per 1.73 sq. m. and 6.5 mmol/l respectively, which are the normal values for said indicators.

The study has revealed a positive effect of the pharmaceutical composition comprising poloxamer-188 on the filtering function of the kidneys after oral administration to the subject; furthermore, no side effects have been found.

The present invention is illustrated by the above examples, which are not intended to limit in any way the subject matter of the present invention. The duration of treatment with a pharmaceutical composition comprising poloxamer-188 is 1-6 months, and each single daily dose of the pharmaceutical composition may comprise poloxamer-188 in the range from 8.6 to 90.0 mg/kg of body weight of the subject.

Thus, a pharmaceutical composition for improving the filtering function of kidneys is developed, the components of which ensure the achievement of the technical result consisting in a substantial reduction in side effects resulting from its use in comparison with the closest analogue.

The invention claimed is:

1. A method for improving the filtering function of the kidneys of a subject, comprising administering a composition of poloxamer-188 as a pharmacologically active substance and at least one excipient; wherein the single daily dose of poloxamer-188 is from 8.6 to 90.0 mg/kg of body weight of the subject.

2. The method of claim 1, wherein the composition is in the form of a solution for oral administration.

3. The method of claim 1, wherein the subject is a mammal.

4. The method of claim 3, wherein the composition is administered to a mammal on a daily basis for 6 months.

* * * * *